(12) United States Patent
Fukuhara

(10) Patent No.: US 9,192,547 B2
(45) Date of Patent: Nov. 24, 2015

(54) WATER-IN OIL EMULSIFIED SUNSCREEN COSMETIC

(75) Inventor: Kazuto Fukuhara, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/240,145

(22) PCT Filed: Jul. 2, 2012

(86) PCT No.: PCT/JP2012/066868
§ 371 (c)(1),
(2), (4) Date: Feb. 21, 2014

(87) PCT Pub. No.: WO2013/031374
PCT Pub. Date: Mar. 7, 2013

(65) Prior Publication Data
US 2014/0205552 A1    Jul. 24, 2014

(30) Foreign Application Priority Data

Aug. 26, 2011 (JP) .................................. 2011-184241

(51) Int. Cl.
| | | |
|---|---|---|
| *A61K 8/06* | (2006.01) | |
| *A61K 8/29* | (2006.01) | |
| *A61K 8/27* | (2006.01) | |
| *A61Q 17/04* | (2006.01) | |
| *A61K 8/31* | (2006.01) | |
| *A61K 8/63* | (2006.01) | |
| *A61K 8/891* | (2006.01) | |
| *A61K 8/894* | (2006.01) | |
| *A61K 8/92* | (2006.01) | |

(52) U.S. Cl.
CPC . *A61K 8/06* (2013.01); *A61K 8/064* (2013.01); *A61K 8/27* (2013.01); *A61K 8/29* (2013.01); *A61K 8/31* (2013.01); *A61K 8/63* (2013.01); *A61K 8/891* (2013.01); *A61K 8/894* (2013.01); *A61K 8/922* (2013.01); *A61Q 17/04* (2013.01)

(58) Field of Classification Search
CPC ............ A61K 8/064; A61K 8/27; A61K 8/29
See application file for complete search history.

(56) References Cited

U.S. PATENT DOCUMENTS

| | | | | |
|---|---|---|---|---|
| 2006/0024251 | A1* | 2/2006 | Gardel et al. | 424/63 |
| 2010/0055220 | A1* | 3/2010 | Akatsuka et al. | 424/776 |
| 2010/0291011 | A1* | 11/2010 | Ikebe et al. | 424/60 |
| 2012/0201905 | A1* | 8/2012 | Mune et al. | 424/684 |
| 2012/0269875 | A1* | 10/2012 | Tamura et al. | 424/401 |

FOREIGN PATENT DOCUMENTS

| | | | |
|---|---|---|---|
| EP | 1086683 | A1 * | 3/2001 |
| JP | H11-246354 | A | 9/1999 |
| JP | 2002-255738 | A | 9/2002 |
| JP | 2005-232068 | A | 9/2005 |
| JP | 2008-050271 | A | 3/2008 |
| JP | 2008-063330 | A | 3/2008 |
| JP | 2009-256268 | A | 11/2009 |
| JP | 2010-059136 | A | 3/2010 |
| JP | 2010-222349 | A | 10/2010 |
| JP | 2010-265225 | A | 11/2010 |
| JP | 2011-126832 | A | 6/2011 |
| WO | WO 2009104353 | A1 * | 8/2009 |

OTHER PUBLICATIONS

The International Bureau of WIPO, "Notification of Transmittal of Copies of Translation of the International Preliminary Report on Patentability," issued in International Application No. PCT/JP2012/066868, of which U.S. Appl. No. 14/240,145 is a U.S. national phase entry, with a date of mailing of Mar. 13, 2014.

* cited by examiner

*Primary Examiner* — Susan Tran
*Assistant Examiner* — Jessica Worsham

(57) ABSTRACT

The present invention provides a water-in-oil emulsified sunscreen cosmetic containing the following (a) through (e):
(a) hydrophobized zinc oxide and hydrophobized titanium dioxide: 10-30 wt %;
(b) lipophilic nonionic surfactant: 0.5-5 wt %;
(c) one, two or more oil components selected from a group consisting of di(phytosteryl/2-octyldodecyl)N-lauroyl-L-glutamate, phytosteryl macadamiate, and cholesteryl macadamiate: 1-5 wt %;
(d) volatile silicone oil and/or hydrocarbon oil: 10-40 wt %; and
(e) water: 5-30 wt %.
The object of the present invention is to improve the poor texture due to a large blend ratio of the ultraviolet scattering agent powder and the poor washability due to the presence of the ultraviolet scattering agent powder in a water-in-oil emulsified sunscreen cosmetic into which hydrophobized zinc oxide and hydrophobized titanium dioxide are blended as ultraviolet scattering agent powder.

4 Claims, 1 Drawing Sheet

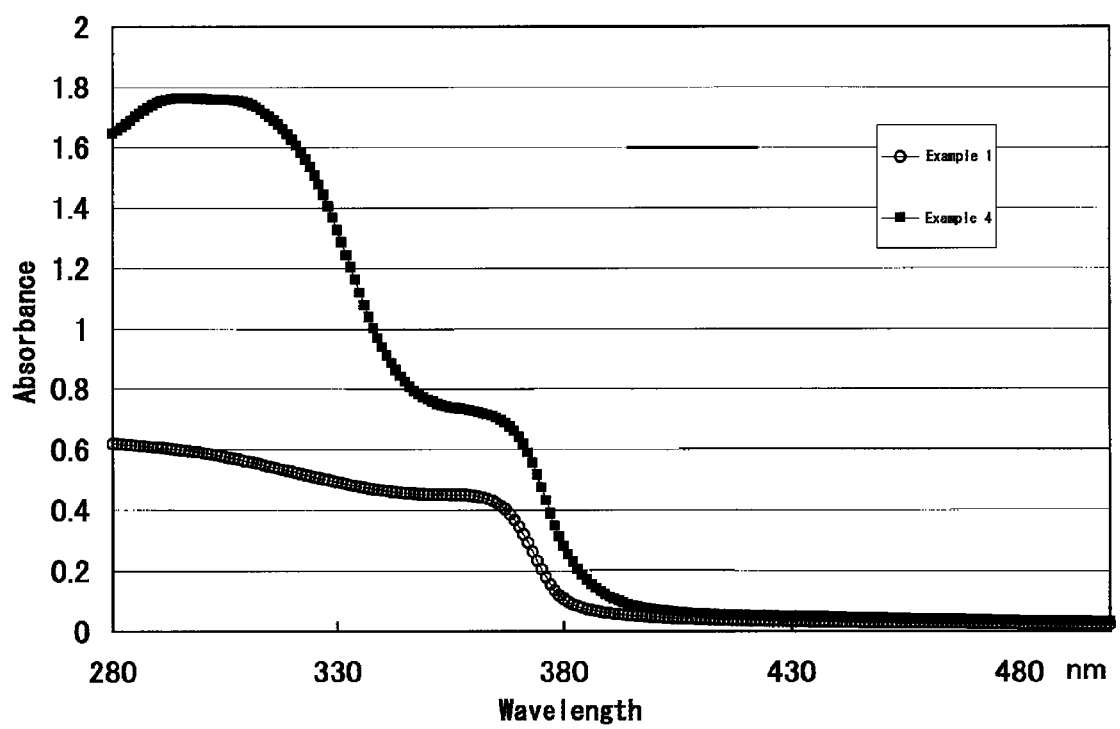

WATER-IN OIL EMULSIFIED SUNSCREEN COSMETIC

CROSS REFERENCE TO RELATED APPLICATIONS

This patent application is a U.S. national stage application under 35 U.S.C. §371 of International Patent Application No. PCT/JP2012/066868 filed on Jul. 2, 2012, which claims the benefit of foreign priority to Japanese Patent Application No. JP 2011-184241 filed on Aug. 26, 2011, the disclosures of all of which are hereby incorporated by reference in their entireties. The International Application was published in Japanese on Mar. 7, 2013, as International Publication No. WO 2013/031374 A1 under PCT Article 21(2).

TECHNICAL FIELD

The present invention relates to a water-in-oil emulsified sunscreen cosmetic. More specifically, it relates to a water-in-oil emulsified sunscreen cosmetic into which a large amount of hydrophobized zinc oxide and hydrophobized titanium dioxide is blended as ultraviolet scattering agent powder in a blend ratio that manifests a sufficient ultraviolet protection ability, wherein poor texture due to a high blend ratio of the ultraviolet scattering agent powder and poor washability due to the addition of the ultraviolet scattering agent powder are improved.

BACKGROUND ART

As shown in Patent Document 1, water-in-oil emulsified sunscreen cosmetics that contain an ultraviolet scattering agent are well known.

However, since Patent Document 1 is a water-in-oil emulsified composition, as many water-in-oil emulsified sunscreen cosmetics are, it has advantages such as good spreadability and superior water resistance; and, Patent Document 1 discloses a sunscreen cosmetic that can achieve a high SPF value without blending in a large amount of an ultraviolet scattering agent, which would cause squeakiness and/or white haze. However, Patent Document 1 still does not provide a water-in-oil emulsified sunscreen cosmetic into which a large amount of an ultraviolet scattering agent can be blended. That is, it is avoiding the technical issue of blending in a large amount of an ultraviolet scattering agent and, in view of the texture, the blend ratio of the ultraviolet scattering agent is limited to 5 wt % or less. Since the blend ratio of the ultraviolet scattering agent is limited, a sufficient amount of the ultraviolet absorbent needs to be blended in.

Also, Patent Document 2 discloses an oil-in-water or water-in-oil emulsified sunscreen cosmetic comprising (a) isodecyl neopentanoate, (b) an ultraviolet absorbent, (c) an ultraviolet scattering agent, and (d) a silicone oil, and it mentions that (c) ingredient is zinc oxide and/or titanium dioxide. The object of the invention of Patent Document 2 is to provide a sunscreen cosmetic that sufficiently manifests the superior ultraviolet blocking effect of the ultraviolet absorbent and the ultraviolet scattering agent, is absorbed well into the skin and devoid of stickiness, i.e., has superior texture, and that is easy to remove from the skin after use (good washability).

Patent Document 3 discloses a water-in-oil emulsified sunscreen cosmetic characteristically comprising (a) a specific hydrophobized zinc oxide powder, (b) volatile silicone, (c) a polyoxyalkylene-modified organopolysiloxane, and (d) water for the purpose of providing an emulsified sunscreen having superior texture by reducing stickiness due to the presence of the hydrophobized powder by stably blending, as an ultraviolet scattering agent, hydrophobized powder having the prominent effect of low oil absorption and a low apparent specific volume. And, it states that, for the hydrophobic powder for the ultraviolet scattering agent, titanium dioxide and zinc oxide are used but that zinc oxide, which has a lower refractive index, is being used more in recent years for transparency at the time of application.

On the other hand, Patent Document 4 discloses a water-in-oil or oil-in-water sunscreen cosmetic that does not contain the ultraviolet scattering agent composed of zinc oxide and/or titanium dioxide for the purpose of providing a sunscreen cosmetic that makes it easy to remove staining from the secondary adhesion on clothing.

PRIOR ART DOCUMENTS

Patent Documents

Patent Document 1: JP 2011-126832 A
Patent Document 2: JP 2010-222349 A
Patent Document 3: JP 2005-232068 A
Patent Document 4: JP 2010-059136 A

SUMMARY OF THE INVENTION

Problem that the Present Invention Aims to Solve

The object of the present invention is to provide a water-in-oil emulsified sunscreen cosmetic into which a large amount of hydrophobized zinc oxide and hydrophobized titanium dioxide is blended as ultraviolet scattering agent powder in a blend ratio that manifests sufficient ultraviolet protection ability, wherein poor texture due to a high blend ratio of the ultraviolet scattering agent powder and poor washability due to the addition of the ultraviolet scattering agent powder are improved.

Means to Solve the Problem

That is, the invention provides a water-in-oil emulsified sunscreen cosmetic characteristically comprising the following (a) through (e):
(a) Hydrophobized zinc oxide and hydrophobized titanium dioxide: 10-30 wt %
(b) Lipophilic nonionic surfactant: 0.5-5 wt %
(c) One, two or more oil components selected from a group consisting of di(phytosteryl/2-octyldodecyl)N-lauroyl-L-glutamate, phytosteryl macadamiate, and cholesteryl macadamiate: 1-5 wt %
(d) Volatile silicone oil and/or hydrocarbon oil: 10-40 wt %
(e) Water: 5-30 wt %

Also, the present invention provides the aforementioned water-in-oil emulsified sunscreen cosmetic wherein the lipophilic nonionic surfactant is a polyoxyethylene/methylpolysiloxane copolymer.

Effects of the Invention (1) By blending in a large amount of the hydrophobized zinc oxide and hydrophobized titanium dioxide as the ultraviolet scattering agent, a water-in-oil emulsified sunscreen cosmetic that manifests sufficient ultraviolet protection ability can be achieved. Therefore, there is no need to blend in an ultraviolet absorbent, which is a significant characteristic and advantage of the present invention. Even if an ultraviolet absorbent was to be blended in, a small blend ratio would be sufficient so it is suitable for blending in a small amount of a slightly soluble ultraviolet absorbent.

(2) The poor texture due to a large blend ratio of the ultraviolet scattering agent powder can be improved.

(3) The poor washability due to the addition of the ultraviolet scattering agent powder can be improved.

BRIEF DESCRIPTION OF THE DRAWINGS

FIG. 1 is the absorbance spectra of Examples 1 and 4.

THE EMBODIMENTS OF THE PRESENT INVENTION

Details of the present invention are described below.

(a) Hydrophobized Zinc Oxide and Hydrophobized Titanium Dioxide

For the ultraviolet scattering agent having sufficient ultraviolet protection ability, zinc oxide and titanium dioxide powders are blended into the water-in-oil emulsified sunscreen cosmetic of the present invention. In the present invention, fine particle titanium dioxide and fine particle zinc oxide having an average particle size of 10-100 nm, more preferably 10-50 nm, are preferable. The average particle size is measured with a usual method such as the number average diameter derived from image analysis of transmission electron microscope images.

The hydrophobized zinc oxide and hydrophobized titanium dioxide are obtained by hydrophobizing zinc oxide and titanium dioxide powders. Said hydrophobized powder exists dispersed in the oil of the water-in-oil emulsified sunscreen cosmetic. The type of the hydrophobizing agent is not limited; examples include fatty acids, higher fatty acids, higher alcohols, hydrocarbons, triglyceride, esters, silicone oils, silicone resins, and fluorine compounds.

Examples of the hydrophobizing agent preferably used in the present invention include alkyltriethoxysilane, alkyltrimethoxysilane, perfluoroalkyl phosphate, (alkyl acrylate/dimethicone) copolymer, dextrin palmitate, triethoxysilylethyl polydimethylsiloxyethyl dimethicone, methicone, dimethicone, high polymer silicone, and sodium acryloyldimethyltaurate/methacrylamide laurate copolymer.

Particularly for zinc oxide, the octyltrimethoxysilane treatment and the silicone (dimethicone/hydro dimethicone) treatment are preferable.

For titanium dioxide, the sodium acryloyldimethyltaurate/methacrylamide laurate copolymer treatment and the stearic acid/aluminum oxide treatment are particularly preferable.

The method for the hydrophobizing treatment is not limited in particular; a surface treatment is conducted following a conventional method. For example, zinc oxide is mixed and stirred for a prescribed amount of time in octyltriethoxysilane and/or dimethylpolysiloxane, followed by filtration, to obtain zinc oxide hydrophobized with octyltriethoxysilane and/or dimethylpolysiloxane. For the dimethylpolysiloxane, a liquid form that can be used for the hydrophobizing treatment is used.

The blend ratio of (a) hydrophobized zinc oxide and hydrophobized titanium dioxide is 10-30 wt %, preferably 12-25 wt %, relative to the total amount of the water-in-oil emulsified sunscreen cosmetic.

(b) Lipophilic Nonionic Surfactant

Examples of the lipophilic nonionic surfactant used in the present invention include sorbitan fatty acid esters (for example, sorbitan mono oleate, sorbitan mono isostearate, sorbitan mono laurate, sorbitan mono palmitate, sorbitan mono stearate, sorbitan sesqui oleate, sorbitan trioleate, diglycerol sorbitan penta-2-ethylhexylate, and diglycerol sorbitan tetra-2-ethylhexylate); glycerin fatty acid esters and polyglycerin fatty acid esters (for example, mono-cottonseed oil fatty acid glycerin, glyceryl monoerucate, glycerin sesquioleate, glyceryl monostearate, α,α'-glyceryl oleate pyroglutamate, and glyceryl mono stearate mono malate); propylene glycol fatty acid esters (for example, propylene glycol monostearate); POE castor oil/POE hydrogenated castor oil derivatives; glycerin alkylethers; and polyoxyethylene/methylpolysiloxane copolymers.

In the present invention, it is particularly preferable to use a polyoxyethylene/methylpolysiloxane copolymer in order to provide a stable emulsion. For the polyoxyethylene/methylpolysiloxane copolymer, a commercial product named "KF-6028" from Shin-Etsu Chemical Co., Ltd. can be used preferably.

A preferable blend ratio of (b) lipophilic nonionic surfactant is 0.5-5 wt %, more preferably 0.5-3 wt %, relative to the total amount of the water-in-oil emulsified sunscreen cosmetic.

(c) One, Two or More Oil Components Selected from a Group Consisting of Di(Phytosteryl/2-Octyldodecyl)N-Lauroyl-L-Glutamate, Phytosteryl Macadamiate, and Cholesteryl Macadamiate The oil component used in the present invention comprises one, two or more oil components selected from a group consisting of di(phytosteryl/2-octyldodecyl)N-lauroyl-L-glutamate, phytosteryl macadamiate, and cholesteryl macadamiate, and this is the oil component that constitutes the oil phase of the outer phase of the water-in-oil emulsified sunscreen cosmetic. For these oil components, commercial products can be used.

Di(phytosteryl/2-octyldodecyl)N-lauroyl-L-glutamate is particularly preferable.

In the present invention, although the detailed mechanism is not understood, it is speculated that the oil component in said ingredient (c) and (d) volatile silicone oil and hydrocarbon oil constitute the oil phase of the water-in-oil emulsified sunscreen cosmetic and the ultraviolet scattering agent composed of (a) hydrophobized zinc oxide and hydrophobized titanium dioxide exists dispersed in said oil phase, which improves both the poor texture due to a large blend ratio of said ultraviolet scattering agent powder and the poor washability due to the presence of the ultraviolet scattering agent powder.

The blend ratio of "(c) one, two or more oil components selected from a group consisting of di(phytosteryl/2-octyldodecyl)N-lauroyl-L-glutamate, phytosteryl macadamiate, and cholesteryl macadamiate" is 1-5 wt %, preferably 1-3 wt %, relative to the total amount of the water-in-oil emulsified sunscreen cosmetic.

(d) Volatile Silicone Oil and/or Hydrocarbon Oil

For the volatile silicone oil used in the present invention, dimethylpolysiloxane and cyclic polysiloxane (for example, octamethylcyclotetrasiloxane, decamethylcyclopentasiloxane, and dodecamethylcyclohexasiloxane), for example, can be used.

Examples of the hydrocarbon oil used in the present invention include liquid paraffin, ozocerite, squalane, pristane, paraffin, squalene, and petrolatum.

In the present invention, both the volatile silicone oil and the hydrocarbon oil or just one of them can be used. Also, two or more types of volatile silicone oil and/or two or more types of hydrocarbon oil may be used.

Said oil component is an oil component that constitutes the oil phase of the water-in-oil emulsified sunscreen cosmetic.

The blend ratio of (d) volatile silicone oil and/or hydrocarbon oil is 10-40 wt %, preferably 20-40 wt %, relative to the total amount of the water-in-oil emulsified sunscreen cosmetic.

The oil component that constitutes the oil phase of the water-in-oil emulsified sunscreen cosmetic may be just the aforementioned ingredient (c) and ingredient (d), but any other oil component can also be blended in as well.

For example, liquid fats and oils, solid fats and oils, waxes, higher fatty acids, higher alcohols, ester oils, and silicone oils can be blended in as appropriate.

(e) Water

Water used in the present invention is an ingredient that constitutes the water phase of the water-in-oil emulsified sunscreen cosmetic. Its blend ratio is 5-30 wt % relative to the total amount of the water-in-oil emulsified sunscreen cosmetic.

In the water-in-oil emulsified sunscreen cosmetic of the present invention, the mass ratio of the water phase (including water soluble ingredients dissolved in water) and the oil phase (including ingredients dissolved or dispersed in the oil component) is in the range of (water phase):(oil phase)=2:8-1:9.

(f) Ultraviolet Absorbent

The water-in-oil emulsified sunscreen cosmetic of the present invention, having a high blend ratio of the ultraviolet scattering agent, can manifest sufficient ultraviolet protection ability without the presence of an ultraviolet absorbent, which is its characteristic and advantage. Any ultraviolet absorbent can obviously be blended in as well. Since the present invention has sufficient ultraviolet protection ability, it has the advantage of allowing a slightly soluble ultraviolet absorbent to be blended in stably if a small amount of the ultraviolet absorbent is to be blended in.

For the ultraviolet absorbent, specifically, (1) benzoic acid-type ultraviolet absorbents, (2) anthranilic acid-type ultraviolet absorbents, (3) salicylic acid-type ultraviolet absorbents, (4) cinnamic acid-type ultraviolet absorbents, (5) triazine-type ultraviolet absorbents, and (6) other ultraviolet absorbents can be blended in.

In addition to the aforementioned essential ingredients, other ingredients usually used in cosmetics can be blended in as appropriate into the water-in-oil emulsified sunscreen cosmetic of the present invention as long as the effect of the present invention is not adversely affected; examples of such ingredients include humectants, thickeners, powders, alcohols, natural polymers, synthetic polymers, sugars, antioxidants, buffers, various extracts, stabilizers, preservatives, pigments, and perfumes.

The water-in-oil emulsified sunscreen cosmetic of the present invention can be prepared with a conventional method. Usually, an HM mixer and such is used to mix and stir (a) hydrophobized zinc oxide and hydrophobized titanium dioxide with (d) volatile silicone oil and/or hydrocarbon oil, (c) one, two or more oil components selected from a group consisting of di(phytosteryl/2-octyldodecyl)N-lauroyl-L-glutamate, phytosteryl macadamiate, and cholesteryl macadamiate, and (b) a lipophilic nonionic surfactant to prepare the dispersion part. In addition, if other oil components and/or oil-based ingredients are to be blended in (for blending in a lipophilic ultraviolet absorbent, for example), this separate part and the dispersion part are mixed to obtain the oil phase.

The water phase is prepared by mixing (e) water and the water-based ingredients such as ethanol, the thickener, and the humectant. Lastly, the water phase and the oil phase are emulsified with a conventional method to obtain the water-in-oil emulsified sunscreen cosmetic of the present invention.

EXAMPLES

The present invention is described in detail through Examples below, but the invention shall not be limited to them. The blend ratios in the recipes are in relation to the total amount and in mass-percentage units unless specified otherwise.

Using the formulations shown in Table 1 and Table 2, a conventional method was used to prepare emulsions that are water-in-oil emulsified sunscreen cosmetics and the following evaluations were conducted.

TABLE 1

| | Raw material chemical name | Example 1 | Example 2 | Example 3 | Comparative example 1 | Comparative example 2 | Comparative example 3 | Comparative example 4 | Comparative example 5 | Comparative example 6 |
|---|---|---|---|---|---|---|---|---|---|---|
| | Glycerin | 5 | 5 | 5 | 5 | 5 | 5 | 5 | 5 | 5 |
| | 1,3-butylene glycol | 5 | 5 | 5 | 5 | 5 | 5 | 5 | 5 | 5 |
| | Organic modified clay mineral (Product name: Bentone 38 VCG from NL Industries, Inc.) | 0.3 | 0.3 | 0.3 | 0.3 | 0.3 | 0.3 | 0.3 | 0.3 | 0.3 |
| (b) | Polyoxyethylene/methyl-polysiloxane copolymer (Product name: KF-6028 (from Shin-Etsu Chemical Co., Ltd.) | 2 | 2 | 2 | 2 | 2 | 2 | 2 | 2 | 2 |
| | Sorbitan sesquiisostearate | 1 | 1 | 1 | 1 | 1 | 1 | 1 | 1 | 1 |
| | Isostearic acid | 0.5 | 0.5 | 0.5 | 0.5 | 0.5 | 0.5 | 0.5 | 0.5 | 0.5 |
| (d) | Cyclomethicone | 38 | 38 | 38 | 38 | 38 | 38 | 38 | 38 | 38 |
| | Pentaerythrityl tetraethylhexanoate | 2 | 2 | 2 | 2 | 2 | 2 | 2 | 2 | 2 |
| | Dimethicone (6 cs) | 1 | 1 | 1 | 1 | 1 | 1 | 1 | 1 | 3 |
| | Triethylhexanoin | 5 | 5 | 5 | 5 | 5 | 5 | 5 | 7 | 5 |
| (c) | Di(phytosteryl/2-octyldodecyl) N-lauroyl-L-glutamate | 2 | | | 0.5 | | | | | |
| (c) | Phytosteryl macadamiate | | 2 | | | | | | | |
| (c) | Cholesteryl macadamiate | | | 2 | | | | | | |
| | Cetyl ethylhexanoate | | | | | 2 | | | | |

TABLE 1-continued

| | Raw material chemical name | Example 1 | Example 2 | Example 3 | Comparative example 1 | Comparative example 2 | Comparative example 3 | Comparative example 4 | Comparative example 5 | Comparative example 6 |
|---|---|---|---|---|---|---|---|---|---|---|
| | Hydrogenated polydecene | | | | | | 2 | | | |
| | Squalane | | | | | | | 2 | | |
| (a) | Octyltrimethoxysilane-treated zinc oxide (20 nm) | 10 | 10 | 10 | 10 | 10 | 10 | 10 | 10 | 10 |
| (a) | Sodium acryloyldimethyltaurate/methacrylamide laurate copolymer-treated titanium dioxide (10-30 nm) | 4 | 4 | 4 | 4 | 4 | 4 | 4 | 4 | 4 |
| | Methyl polymethacrylate | 4 | 4 | 4 | 4 | 4 | 4 | 4 | 4 | 4 |
| | Polymethylsilsesquioxane | 1 | 1 | 1 | 1 | 1 | 1 | 1 | 1 | 1 |
| | Phenoxy ethanol | 0.5 | 0.5 | 0.5 | 0.5 | 0.5 | 0.5 | 0.5 | 0.5 | 0.5 |
| | Sodium metaphosphate | 0.1 | 0.1 | 0.1 | 0.1 | 0.1 | 0.1 | 0.1 | 0.1 | 0.1 |
| | Purified water | Balance | Balance | Balance | Balance | Balance | Balance | Balance | Balance | Balance |
| UV protection ability | | ○ | ○ | ○ | ○ | ○ | ○ | ○ | ○ | ○ |
| Texture | | ⊚ | ○ | ○ | ○ | Δ | Δ | X | Δ | Δ |
| Washability | | ○ | ○ | ○ | Δ | Δ | X | X | Δ | Δ |

"UV Protection Ability"

A sample prepared using each formulation was applied on a PMMA plate (5 cm×5 cm) in the amount of 0.75 mg/cm². The absorbance in the range of 290-500 nm was measured by using a spectrophotometer (U-4100 from Hitachi High-Technologies Corporation) and an absorbance spectrum comparison between Examples and Comparative examples was conducted.

<Evaluation Criteria>

○: The content of the ultraviolet scattering agent is the same as in Example 1 (total of 14 wt %) and the absorbance spectrum is similar to that of Example 1. Therefore, the UV protection ability is as superior as Example 1.

x: The ultraviolet scattering agent content is less than 10 wt % and the UV protection ability is inferior.

<Results>

The absorbance spectrum of Example 1 is shown in FIG. 1.

The absorbance spectra of Examples 2-3 and Comparative examples 1-6 were similar to the absorbance spectrum of Example 1, and the evaluations for Examples 1-3 and Comparative examples 1-6 are all "○", indicating that their UV protection abilities are equally superior.

That is, each of Examples and Comparative examples in Table 1 contains a sufficient total of 14 wt % of (a) ultraviolet scattering agent powder (octyltrimethoxysilane-treated zinc oxide and sodium acryloyldimethyltaurate/methacrylamide laurate copolymer-treated titanium dioxide) and exhibited a spectrum indicating a high absorbance.

This indicates that the water-in-oil emulsified sunscreen cosmetic of the present invention manifests a very high UV protection ability. It is thus indicated that the present invention has a superior advantage of manifesting superior UV protection ability even when an ultraviolet absorbent is not blended in.

"Texture"

An actual use test with a panel of ten specialists (the sunscreen cosmetics of Examples and Comparative examples were applied on the upper arm) was conducted to evaluate whether the comprehensive texture is superior, i.e., powder is not grainy but smooth to the touch.

<Evaluation Criteria>

⊚: 7 or more of the 10 reported superior texture.

○: 5 or more and less than 7 of the 10 reported superior texture.

Δ: 3 or more and less than 5 of the 10 reported superior texture.

x: 2 or less of the 10 reported superior texture.

<Results>

Each of Examples 1-3 and Comparative example 1 turned out to manifest superior texture compared with Comparative examples 2-6, despite the fact that they had a high total blend ratio of the ultraviolet scattering agent(s) of 14 wt %.

Furthermore, Example 1, which used di(phytosteryl/2-octyldodecyl)N-lauroyl-L-glutamate for ingredient (c) turned out to manifest particularly superior texture.

"Washability"

An actual use test was conducted by a panel of 10 specialists. 18 mg of the sunscreen cosmetic of Examples and Comparative examples was applied in a 3 cm×3 cm frame on the upper arm of each panelist, manipulated to be absorbed, and dried for 30 minutes. After this, the application site was washed with a commercial hand cleansing agent (soap). 15 minutes after the washing, the sensation of residual cosmetic was checked by touching the skin.

<Evaluation Criteria>

○: a 6 or more of the 10 did not feel the residual cosmetic.

Δ: 3 or more of the 10 did not feel the residual cosmetic.

x: 2 or less of the 10 did not feel the residual cosmetic.

<Results>

It turned out that Examples 1-3 are all superior to Comparative examples 1-6 in terms of washability. It turned out that the washability of Comparative example 1 is inferior to Examples 1-3 because the blend ratio of di(phytosteryl/2-octyldodecyl)N-lauroyl-L-glutamate, ingredient (c), was 0.5 wt %.

TABLE 2

| | Raw material chemical name | Example 4 | Example 5 | Example 6 | Comparative example 7 | Comparative example 8 | Comparative example 9 | Comparative example 10 | Comparative example 11 |
|---|---|---|---|---|---|---|---|---|---|
| | Glycerin | 5 | 5 | 5 | 5 | 5 | 5 | 5 | 5 |
| | Dipropylene glycol | 7 | 7 | 7 | 7 | 7 | 7 | 7 | 7 |
| | PEG/PPG-17/4 dimethyl ether | 3 | 3 | 3 | 3 | 3 | 3 | 3 | 3 |
| (b) | Polyoxyethylene/methylpolysiloxane copolymer (Product name: KF-6028 (from Shin-Etsu Chemical Co., Ltd.) | 0.6 | 0.6 | 0.6 | 0.6 | 0.6 | 0.6 | 0.6 | 0.6 |
| | Sorbitan sesquiisostearate | 0.5 | 0.5 | 0.5 | 0.5 | 0.5 | 0.5 | 0.5 | 0.5 |
| | Triethanolamine | 1.5 | 1.5 | 1.5 | 1.5 | 1.5 | 1.5 | 1.5 | 1.5 |
| (d) | Cyclomethicone | 18 | 18 | 18 | 18 | 18 | 18 | 18 | 18 |
| (d) | Isododecane | 5 | 5 | 5 | 5 | 5 | 5 | 5 | 5 |
| | Isostearic acid | 0.3 | 0.3 | 0.3 | 0.3 | 0.3 | 0.3 | 0.3 | 0.3 |
| (c) | Di (phytosteryl/2-octyldodecyl) N-lauroyl-L-glutamate | 1.5 | | 5 | 7 | | | | |
| (c) | Phytosteryl macadamiate | | 1.5 | | | | | | |
| | Pentaerythrityl tetraethylhexanoate | | | | | | 1.5 | | |
| | macadamia nut oil | | | | | | | 1.5 | |
| | Ethylhexyl palmitate | | | | | | | | 1.5 |
| | Cetyl ethylhexanoate | 3 | 3 | 3 | 3 | 3 | 3 | 3 | 3 |
| | Dimethicone (6 cs) | 5 | 5 | 5 | 5 | 5 | 5 | 5 | 5 |
| | Polypropylene glycol | 2 | 2 | 2 | 2 | 2 | 2 | 2 | 2 |
| | Ethylhexyl p-methoxycinnamate | 7.5 | 7.5 | 7.5 | 7.5 | 7.5 | 7.5 | 7.5 | 7.5 |
| | Phenylbenzimidazole sulfonic acid | 2.5 | 2.5 | 2.5 | 2.5 | 2.5 | 2.5 | 2.5 | 2.5 |
| (a) | Stearic acid/aluminum oxide-treated titanium dioxide (10-30 nm) | 4 | 4 | 4 | 4 | 4 | 4 | 4 | 4 |
| (a) | Dimethicone/hydro dimethicone-treated zinc oxide (20 nm) | 15 | 15 | 15 | 15 | 15 | 15 | 15 | 15 |
| | Methyl polymethacrylate | 3 | 3 | 3 | 3 | 3 | 3 | 3 | 3 |
| | Polymethylsilsesquioxane | 2 | 2 | 2 | 2 | 2 | 2 | 2 | 2 |
| | Talc | 3 | 3 | 3 | 3 | 3 | 3 | 3 | 3 |
| | Vitamin E derivative | 0.05 | 0.05 | 0.05 | 0.05 | 0.05 | 0.05 | 0.05 | 0.05 |
| | Gamma-oryzanol | 0.05 | 0.05 | 0.05 | 0.05 | 0.05 | 0.05 | 0.05 | 0.05 |
| | EDTA | 0.2 | 0.2 | 0.2 | 0.2 | 0.2 | 0.2 | 0.2 | 0.2 |
| | Purified water | Balance | Balance | Balance | Balance | Balance | Balance | Balance | Balance |
| | Stability | ○ | ○ | ○ | X | ○ | ○ | ○ | ○ |
| | UV protection ability | ○ | ○ | ○ | — | ○ | ○ | ○ | ○ |
| | Texture | ◎ | ○ | ○ | — | Δ | X | X | X |
| | Washability | ○ | ○ | ○ | — | Δ | Δ | X | X |

"Stability"

The emulsion was put into a sample tube right after preparation, and visual observation after leaving it alone at 50° C. for one month was conducted.

<Evaluation Criteria>

○: The oil phase is in a compatibilized, colorless and transparent, and stable state.

x: The oil phase ingredients don't mix with each other and white turbidity occurs, which is not a stable state.

<Results>

It turned out that Examples 4-6 and Comparative examples 8-11 were superior in terms of stability. It turned out that only Comparative example 7, for which the blend ratio of di(phytosteryl/2-octyldodecyl)N-lauroyl-L-glutamate, ingredient (c), was 7 wt %, was inferior in terms of stability.

Since Comparative example 7 had inferior stability and was not in a stable state, the following tests for UV protection ability, texture, and washability were not conducted on it.

"UV Protection Ability"

A sample prepared using each formulation was applied on a PMMA plate (5 cm×5 cm) in the amount of 0.75 mg/cm$^2$. The absorbance in the range of 290-500 nm was measured by using a spectrophotometer (U-4100 from Hitachi High-Technologies Corporation) and an absorbance spectrum comparison between Examples and Comparative examples was conducted.

<Evaluation Criteria>

○: The blend ratio of the ultraviolet scattering agent was the same as in Example 4 (total of 19 wt %) and the absorbance spectrum was similar to that of Example 4. Therefore, the UV protection ability is as superior as Example 4.

x: The ultraviolet scattering agent content is less than 10 wt % and the UV protection ability is inferior.

<Results>

The absorbance spectrum of Example 4 is shown in FIG. 1.

The absorbance spectra of Examples 5-6 and Comparative examples 8-11 were similar to the absorbance spectrum of Example 4, and the evaluations for Examples 4-6 and Comparative examples 8-11 are all "○", indicating that their UV protection abilities are equally superior.

That is, each of Examples and Comparative examples in Table 2 contains a sufficient total of 19 wt % of (a) ultraviolet scattering agent powder (stearic acid/aluminum oxide-treated titanium dioxide and dimethicone/hydro dimethicone-treated zinc oxide) and exhibited a spectrum indicating a high absorbance.

This indicates that the water-in-oil emulsified sunscreen cosmetic of the present invention manifests a very high UV protection ability. It is thus indicated that the present invention has a superior advantage of manifesting superior UV protection ability even when an ultraviolet absorbent is not blended in.

"Texture, Washability"

The same testing as in the aforementioned Table 1 was conducted and evaluated the same way.

Regarding texture, each of Examples 4-6 turned out to manifest superior texture compared with Comparative examples 8-11, despite the fact that they had a high total blend ratio of the ultraviolet scattering agent of 19 wt %. Furthermore, Example 4, which used di(phytosteryl/2-octyldodecyl) N-lauroyl-L-glutamate for ingredient (c) turned out to manifest particularly superior texture.

Regarding washability, it turned out that Examples 4-6 are all superior to Comparative examples 8-11 in terms of washability.

Other Examples of the present invention are shown below. They are all water-in-oil emulsified sunscreen cosmetics that are superior in terms of stability, UV protection ability, texture, and washability.

Example 7

W/O Sunscreen Cosmetic (Emulsion)

| Ingredient | wt % |
| --- | --- |
| (1) Glycerin | 5 |
| (2) 1,3-butylene glycol | 5 |
| (3) Organic modified clay mineral (Product name: Bentone 38 VCG from NL Industries, Inc.) | 0.3 |
| (4) Polyoxyethylene/methylpolysiloxane copolymer (Product name: KF-6028 from Shin-Etsu Chemical Co., Ltd.) | 2 |
| (5) Sorbitan sesquiisostearate | 1 |
| (6) Isostearic acid | 0.5 |
| (7) Cyclomethicone | 38 |
| (8) Triethylhexanoin | 2 |
| (9) Pentaerythrityl tetraethylhexanoate | 5 |
| (10) Dimethicone (6 cs) | 1 |
| (11) Di(phytosteryl/2-octyldodecyl) N-lauroyl-L-glutamate | 2 |
| (12) Octyltrimethoxysilane-treated zinc oxide (20 nm) | 10 |
| (13) Stearic acid/aluminum oxide-treated titanium dioxide (10-30 nm) | 4 |
| (14) Methyl polymethacrylate | 4 |
| (15) Polymethylsilsesquioxane | 1 |
| (16) Phenoxyethanol | 0.5 |
| (17) Na metaphosphate | 0.1 |
| (18) Purified water | Balance |

<Preparation Method>

(4)-(11) are mixed to prepare the oil phase. (16) is wetted with (2) and, together with (1), mixed with (18) in which (17) is already dissolved (water phase). (3) is added to the oil phase and dispersed with a disper, and then (12)-(15) are similarly dispersed in the oil phase with a disper. Finally, the oil phase and the water phase are mixed and emulsified with an emulsifier.

Example 8

W/O Sunscreen Cosmetic (Emulsion)

| Ingredient | wt % |
| --- | --- |
| (1) Glycerin | 5 |
| (2) Dipropylene glycol | 7 |
| (3) PEG/PPG-17/4 dimethyl ether | 3 |
| (4) Polyether-modified silicone (product name: Silicone SC0938B) | 0.6 |
| (5) Sorbitan sesquiisostearate | 0.5 |
| (6) Triethanolamine | 1.5 |

-continued

| Ingredient | wt % |
| --- | --- |
| (7) Cyclomethicone | 18 |
| (8) Isododecane | 5 |
| (9) Isostearic acid | 0.3 |
| (10) Di(phytosteryl/2-octyldodecyl) N-lauroyl-L-glutamate | 1.5 |
| (11) Cetyl ethylhexanoate | 3 |
| (12) Dimethicone (6 cs) | 5 |
| (13) Polypropylene glycol | 2 |
| (14) Ethylhexyl p-methoxycinnamate | 7.5 |
| (15) Phenylbenzimidazole sulfonic acid | 2.5 |
| (16) Sodium acryloyldimethyltaurate/methacrylamide laurate copolymer-treated titanium dioxide (10-30 nm) | 5 |
| (17) Dimethicone/hydro dimethicone-treated zinc oxide (20 nm) | 15 |
| (18) Methyl polymethacrylate | 3 |
| (19) Polymethylsilsesquioxane | 2 |
| (20) Talc | 3 |
| (21) EDTA | 0.2 |
| (22) Purified water | Balance |

<Preparation Method>

(4) and (5) are added to the mixture of (7)-(14) to prepare the oil phase. Next, (21) is dissolved into (22). (6) is added to this, into which (15) is dissolved and (1)-(3) are added (water phase).

(16)-(20) are added to the oil phase, dispersed with a disper, mixed with the water phase, and emulsified with an emulsifier.

INDUSTRIAL APPLICABILITY

The water-in-oil emulsified sunscreen cosmetic of the present invention is a new and useful invention that manifests superior ultraviolet protection ability, superior texture and washability.

The water-in-oil emulsified sunscreen cosmetic of the present invention is preferably used as sunscreen emulsion and/or sunscreen cream.

The invention claimed is:

1. A water-in-oil emulsified sunscreen cosmetic comprising the following (a) through (e):
    (a) hydrophobized zinc oxide and hydrophobized titanium dioxide in a combined amount of 10-30 wt %;
    (b) lipophilic nonionic surfactant in an amount of 0.5-5 wt %;
    (c) oil component di(phytosteryl/2-octyldodecyl)N-lauroyl-L-glutamate in an amount of 1-2 wt %;
    (d) volatile silicone oil and/or hydrocarbon oil in a combined amount of 10-40 wt %; and
    (e) water in an amount of 5-30 wt %.

2. The water-in-oil emulsified sunscreen cosmetic of claim 1 wherein the lipophilic nonionic surfactant (b) is a polyoxyethylene/methylpolysiloxane copolymer.

3. The water-in-oil emulsified sunscreen cosmetic of claim 1 wherein the hydrophobized zinc oxide and hydrophobized titanium dioxide (a) are hydrophobized fine particle zinc oxide and hydrophobized fine particle titanium dioxide having an average particle size of 10-100 nm.

4. The water-in-oil emulsified sunscreen cosmetic of claim 2 wherein the hydrophobized zinc oxide and hydrophobized titanium dioxide (a) are hydrophobized fine particle zinc oxide and hydrophobized fine particle titanium dioxide having an average particle size of 10-100 nm.

* * * * *